United States Patent [19]

Balassyano

[11] Patent Number: 5,711,949
[45] Date of Patent: Jan. 27, 1998

[54] VISION IMPROVING EYE SOLUTION

[76] Inventor: Eitan Balassyano, 86-05 60th Rd., Apt. 3C, Elmhurst, N.Y. 11373-5515

[21] Appl. No.: 699,419

[22] Filed: Aug. 19, 1996

[51] Int. Cl.[6] ............................................. A61K 35/78
[52] U.S. Cl. ................................. 424/195.1; 514/912
[58] Field of Search ........................ 424/195.1; 514/912

[56] References Cited

PUBLICATIONS

WPIDS 073027, 1993.

*Primary Examiner*—Zohreh Fay
*Attorney, Agent, or Firm*—Michael I. Kroll

[57] ABSTRACT

The present invention relates to a vision improving eye solution (10) comprising: $H_2O$ (12), panax ginseng extractum (14) and microorganisms (16). A method (110) of preparing a vision improving eye solution (10) is described which consists of the following steps: A) sterilizing (112) $H_2O$ (12); B) first mixing (114) panax ginseng extractum (14) into sterilized $H_2O$ (12); C) second mixing (116) panax ginseng extractum (14)/sterilized $H_2O$ (12) with microorganism (16); D) incubating (118) the panax ginseng extractum (14)/sterilized $H_2O$ (12) solution/microorganism (16) in a bottle (20); E) attenuating (120) the microorganism (16); and F) adding (122) NaCl (18) until isotonic. A method (210) of utilizing a vision improving eye solution (10) is also described which consists of the following steps: A) applying (212) vision improving eye solution (10) to each eye; B) mucating (214) of the eyes; c) drying (215) the eyes with a hair dryer for a time period in a range from 10–15 seconds every three days for five consecutive dryings (215), and D) improving (216) vision in the eyes.

3 Claims, 4 Drawing Sheets

110

| sterilizing (112) H2O (12) | 112 |

| first mixing (114) panax ginseng extractum (14) into sterilized H2O (12) | 114 |

| second mixing (116) panax ginseng extractum (14)/sterilized H2O (12) with microorganism (16) | 116 |

| 118 | incubating (118) the panax ginseng extractum (14)/sterilized H2O (12) solution/microorganism (16) |

| 120 | attenuating (120) the microorganism (16) |

| 122 | adding (122) NaCl (18) until isotonic |

212 — applying (212) vision improving eye solution (10) to each eye

214 — mucating (214) of the eyes

215 — drying (215) the eyes with a hair dryer for a time period in a range from 10-15 seconds every three days for five consecutive dryings (215)

216 — improving (216) vision in the eyes

FIG. 3

VISION IMPROVING EYE SOLUTION

BACKGROUND OF THE INVENTION

1. Field of the Invention

The present invention relates to eye solutions. More particularly, the present invention relates to eye solutions with eyesight improving properties.

2. Description of the Prior Art

Currently, eye sight is improved only two ways: a) changing the focal length of the lens by utilizing glasses or contact lenses and b) surgery on the cornea. The present invention discloses and claims a new and unique eye solution and method of preparing the same. The eye solution has the properties of improving eye sight.

Numerous innovations for eye sight improvement means have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a vision improving eye solution consisting of $H_2O$, panax ginseng extractum, and attenuated microorganisms with normal NaCl osmolarity. The vision improving eye solution is applied directly into each eye. The following day after application, the eyes begin to mucate and turn red for 3-4 days with sight improving each day. The sight improvement will last for 3-4 months.

The panax ginseng is a root of araliaceae which is a precious natural product growing in the mountains of the north-eastern provinces of China. The panax ginseng has natural healing properties which are beneficial to sight improvement.

The types of problems encountered in the prior art are eye surgery is extremely costly and permanent. It often must be repeated after several years when the contour of the cornea changes with age. Both glasses and contact lenses are expensive, hard to maintain and cumbersome.

In the prior art, unsuccessful attempts to solve this problem were attempted namely: surgery and artificial focal length changing means. However, the problem was solved by the present invention because the vision improving eye solution contains panax ginseng extractum and an attenuated microorganism which work in conjunction with one another to improve eye sight. The sight is sharply improved after 3-4 days lasting years just like new eyes. The microorganisms utilized are viruses and bacteria of the conjunctivitis nature which are commonly called "pinkeye".

Innovations within the prior art are rapidly being exploited in the field of eye sight improvement methods.

The present invention went contrary to the teaching of the art which teaches surgical and mechanical focal point improvement means.

The present invention solved a long felt need for a simple and inexpensive eye improving means which lacks either mechanical or surgical focal point changing means.

The present invention produced unexpected results namely: eye sight was self adjusting so that when treatment occurs over a period of years, the eye adapts to the change of focal point of the cornea which is a result of aging.

Accordingly, it is an object of the present invention to provide a vision improving eye solution.

More particularly, it is an object of the present invention to provide a vision improving eye solution which comprises $H_2O$.

In keeping with these objects, and with others which will become apparent hereinafter, one feature of the present invention resides, briefly stated, in a vision improving eye solution which comprises panax ginseng extractum.

When the vision improving eye solution is designed in accordance with the present invention, it comprises at least one microorganism which is attenuated.

In accordance with another feature of the present invention, the microorganism is selected from a group consisting of bacteria, virus, and fungi.

Another feature of the present invention is that the vision improving eye solution is at a normal isotonic composition by adding v:v 0.075% NaCl.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

VISION IMPROVING EYE SOLUTION(10)

10—vision improving eye solution (10)
12—$H_2O$
14—panax ginseng extractum (14)
16—microorganism (16)
16A—bacteria (16A)
16B—virus (16B)
16C—fungi (16C)
18—NaCl (18)
20—bottle (20)
20A—bottle cap (20A)
20AA—bottle cap eye dropper (20AA)
22—instructions (22)
24—contents (24)

METHOD (110) OF PREPARING A VISION IMPROVING EYE SOLUTION (10)

110—method (110) of preparing a vision improving eye solution (10)
112—sterilizing (112) $H_2O$ (12)
114—first mixing (114) panax ginseng extractum (14) into sterilized $H_2O$ (12)
116—second mixing (116) panax ginseng extractum (14)/ sterilized $H_2O$ (12) with microorganism (16)
118—incubating (118) the panax ginseng extractum (14)/ sterilized $H_2O$ (12) solution/microorganism (16)
120—attenuating (120) the microorganism (16)
122—adding (122) NaCl (18) until isotonic

METHOD (210) OF UTILIZING A VISION IMPROVING EYE SOLUTION (10)

210—method (210) of utilizing a vision improving eye solution (10)
212—applying (212) vision improving eye solution (10) to each eye
214—mucating (214) of the eyes
215—drying (215) the eyes with a hair dryer for a time period in a range from 10-15 seconds every three days for five consecutive dryings (215)
216—improving (216) vision in the eyes

BRIEF DESCRIPTION OF THE DRAWING

FIG. 2 is a diagrammatic representation of a method of preparing a vision improving eye solution.

FIG. 3 is a diagrammatic representation of a method of utilizing a vision improving eye solution.

DESCRIPTION OF THE PREFERRED EMBODIMENT

Figure 1:
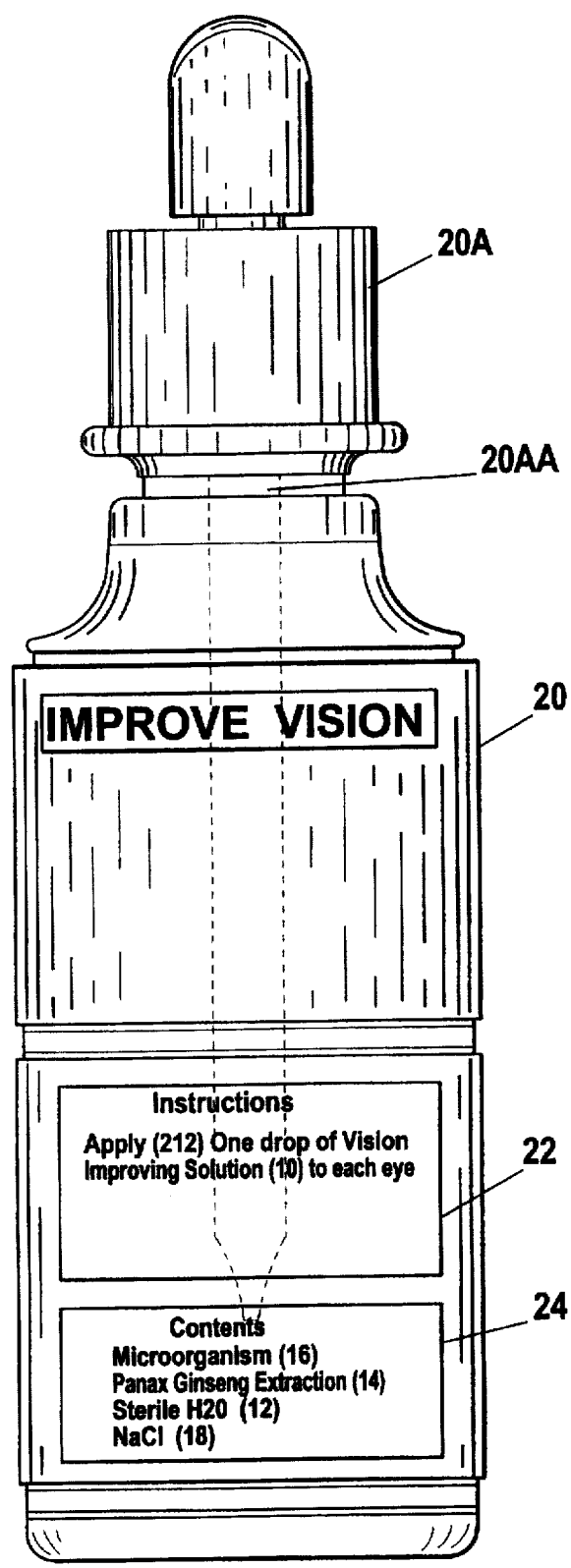
FIG. 1 is a front view of a bottle.

Firstly, referring to FIG. 1 which is a from view of a bottle (20) exhibiting a bottle cap (20A) which comprises a bottle cap eye dropper (20AA), utilized to administer the vision improving eye solution (10), integrally attached thereto. In addition, the bottle (20) my optionally display instructions (22). Furthermore, the bottle (20) may optionally display contents (24).

Referring to FIG. 2 which is a diagrammatic representation of a method (110) of preparing a vision improving eye solution (10) consisting of the following steps:

A) sterilizing (112) $H_2O$ (12);

B) first mixing (114) approximately five drops of panax ginseng extractum (14) into sterilized $H_2O$ (12);

C) second mixing (116) panax ginseng extractum (14)/ sterilized $H_2O$ (12) with microorganism (16);

D) incubating (118) the pane ginseng extractum (14)/ sterilized $H_2O$ (12) solution/microorganism (16) in a sealed container for several months allowing the organism to multiply and become non-viable;

E) attenuating (120) the microorganism (16); and

F) adding (122) NaCl (18) until isotonic.

The vision improving eye solution (10) is manufactured by boiling approximately 25 ml of $H_2O$ (12) and allowing it to cool. Then approximately 10 drops of panax ginseng extractum (14) is then added to the cooled sterilized $H_2O$ (12). The microorganisms (16) are then added to the $H_2O$ (12)/panax ginseng extractum (14) solution for a time period in excess of one month. The longer the time period, the stronger and better the vision improving eye solution (10).

Referring to FIG. 3 which is a diagrammatic representation of a method (210) of utilizing a vision improving eye solution (10) consisting of the following steps:

A) applying (212) vision improving eye solution (10) to each eye;

B) mutating (214) of the eyes;

C) drying (215) the eyes with a hair dryer for a time period in a range from 10–15 seconds every three days for five consecutive dryings (215); and D) improving (2 16) vision in the eyes.

The vision improving eye solution (10) is utilized by placing one drop in each eye. It can also be utilized by mixing it a solution such as coffee or tea and drinking it.

After applying a drop of the vision improving eye solution (10) to each eye, mutating commences the next day lasting 3–4 days. Concurrently, vision improvement occurs lasting from 3–4 months.

Figure 4:
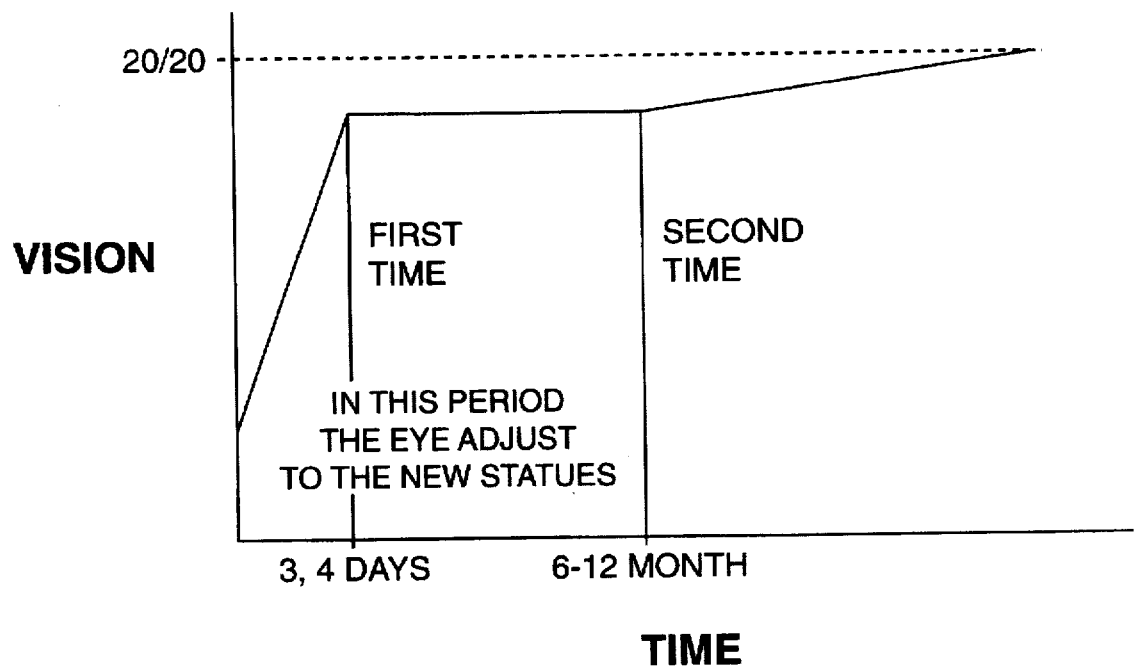
FIG. 4 is a diagrammatic graph of a vision improvement versus time representing a method of utilizing a vision improving eye solution.

Lastly, referring to FIG. 4 which is a diagrammatic graph of a vision improvement versus time representing a method of utilizing a vision improving eye solution (10). When the vision improving eye solution (10) is applied for the first time to the eye in about 3–4 days vision improves dramatically due to eye adjustment. In approximately 6–12 months, the vision improving eye solution (10) is again applied to the eye for a final eye improvement which parallels 20/20 vision. The vision improving eye solution (10) improves either nearsightedness or farsightedness.

It will be understood that each of the elements described above, or two or more together, may also find a useful application in other types of constructions differing from the type described above.

While the invention has been illustrated and described as embodied in a vision improving eye solution, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An eye solution comprising:

A) $H_2O$ containing NaCl;

B) panax ginseng extractum; and

C) microorganisms selected from the group consisting of bacteria, virus, and fungi.

2. A method of preparing an eye solution consisting of the following steps:

A) sterilizing $H_2O$;

B) first mixing panax ginseng extractum into sterilized $H_2O$;

C) second mixing panax ginseng extractum/sterilized $H_2O$ with microorganism selected from a group consisting of bacteria, virus, and fungi;

D) incubating the panax ginseng extractum/sterilized $H_2O$ solution/microorganism in a sealed bottle;

E) attenuating the microorganism; and

F) adding NaCl until isotonic.

3. A method of utilizing an eye solution consisting of the following steps:

A) applying said eye solution to each eye, said eye solution comprising sterilized $H_2O$ with NaCl, panax ginseng extractum, and microorganisms selected from the group consisting of bacteria, virus, and fungi;

B) mucating of the eyes; and

C) drying the eyes with a hair dryer for a time period in a range of 10–15 seconds every three days for five consecutive dryings.

* * * * *